US00PP16493P3

(12) United States Plant Patent
Meilland

(10) Patent No.: US PP16,493 P3
(45) Date of Patent: May 2, 2006

(54) HYBRID TEA ROSE PLANT NAMED 'MEIVANTHOU'

(50) Latin Name: *Rosa hybrida*
Varietal Denomination: Meivanthou

(75) Inventor: Alain A. Meilland, Antibes (FR)

(73) Assignee: C.P. Delaware, Inc., Wilmington, DE (US)

( * ) Notice: Subject to any disclaimer, the term of this patent is extended or adjusted under 35 U.S.C. 154(b) by 154 days.

(21) Appl. No.: 10/851,100

(22) Filed: May 24, 2004

(65) Prior Publication Data

US 2004/0216197 P1 Oct. 28, 2004

Related U.S. Application Data

(63) Continuation of application No. 10/306,206, filed on Nov. 29, 2002, now abandoned, which is a continuation of application No. 09/276,714, filed on Mar. 26, 1999, now abandoned.

(51) Int. Cl.
*A01H 5/00* (2006.01)

(52) U.S. Cl. ..... Plt./140

(58) Field of Classification Search ..... Plt./140
See application file for complete search history.

*Primary Examiner*—Kent Bell
*Assistant Examiner*—W. C. Haas
(74) *Attorney, Agent, or Firm*—Buchanan Ingersoll PC

(57) ABSTRACT

A new and distinct variety of Hybrid Tea rose plant is provided which forms attractive double deep red blossoms with turgescent petals. The buds are large and the blossoms possess no fragrance. The plant exhibits an erect growth habit, and dark green and semi-glossy foliage. Excellent disease resistance particularly with respect to Downey Mildew and Botrytis is exhibited. The new variety is particularly well suited for producing cut flowers under greenhouse growing conditions.

1 Drawing Sheet

Figures 1, 2, 3, 4, 5, 6, 7, 8, 9, 10, 11, 12, 13, 14, 15, 16:
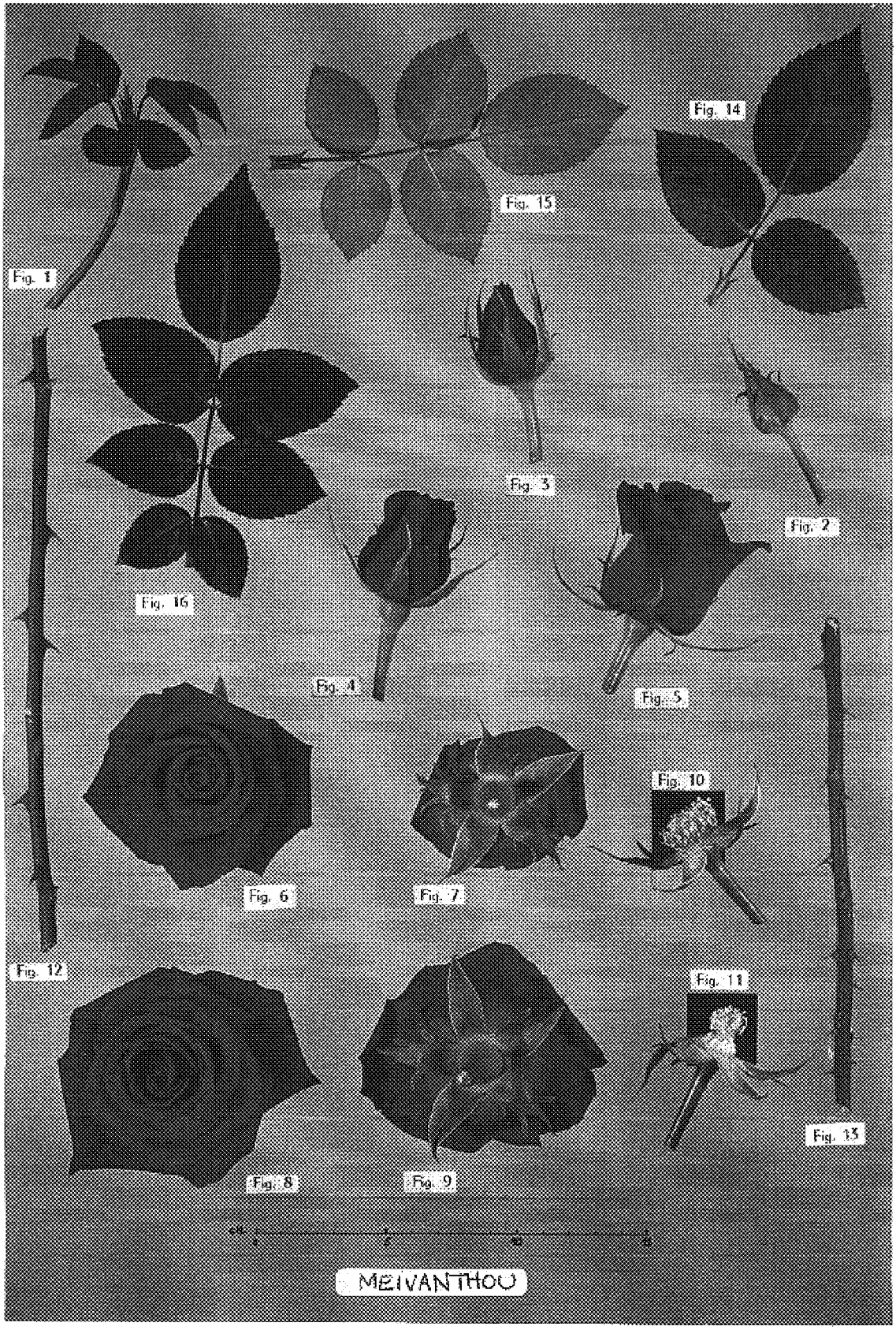

Botanical/commercial classification: *Rosa hybrida*/Hybrid Tea Rose Plant.
Varietal denomination: cv. 'Meivanthou'.

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Keireb' variety (U.S. Plant Pat. No. 8,369). The male parent (i.e., the pollen parent) was the product of the cross of the 'Hilred' variety (U.S. Plant Pat. No. 8,964) and the 'Meigormon' variety (U.S. Plant Pat. No. 8,647). The parentage of the new variety can be summarized as follows:

'Keireb'×('Hilred'×'Meigormon').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms large floral buds;

(b) forms attractive high-centered double deep red blossoms with turgescent petals, (c) exhibits an erect growth habit, (d) exhibits excellent disease resistance particularly with respect to Downey Mildew and Botrytis, and (e) is particularly well suited for the production of cut flowers under greenhouse growing conditions.

The plant exhibits a very uniform and homogeneous appearance.

The new variety well meets the needs of the horticultural industry and exhibits good productivity during cut flower production in a greenhouse.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meivanthou' variety, and is being marketed in the United States under the MAGNUM trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during April while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year-old plants during April while budded on *Rosa indica* understock and growing indoors at Le Cannet des Maures, Var, France. The coloration in common terms precedes reference to the chart in some instances.

Class: Hybrid Tea.

Plant:

*Height.*—When pruned to a height of 85 cm., floral stems of approximately 50 to 80 cm. in length commonly are produced.

*Habit.*—Erect.

Branches:

*Color.*—Young stems: near Green Group 138B. Adult wood: near Green Group 137C.

*Thorns.*—Size: medium (as illustrated). Quantity: fairly numerous. Color: near Greyed-Orange Group 173B on young stems. Configuration: rather straight, elongated, and inflected toward the base on the upper surface, and concave on the under surface.

Leaves:

*Stipules.*—Adnate, pectinate, and rather wide.

*Petioles.*—Upper surface: slightly glandular in nature, and Green Group 139A on the upper surface and Green Group 137C on the under surface. Under surface: light green with a few prickles.

*Leaflets.*—Number: 3, 5 (most often), and 7. Shape: symmetrical with an obtuse base. Serration: regular (as illustrated). Texture: consistent. General appearance: dense, medium green, and semi-glossy. Color (young foliage): Upper surface: near Yellow-Green Group 147A with reddish staining. Under surface: near Greyed-Green Group 191A with reddish staining. Color (adult foliage): Upper surface: near Yellow-Green Group 147A. Under surface: near Greyed-Green Group 191A.

Inflorescence:

*Number of flowers.*—Usually one flower per stem.

*Peduncle.*—Long, and the length is approximately 14 cm. on average and Green Group 143B in coloration.

*Sepals.*—Upper surface: tomentose and Green Group 138B and 138C in coloration. Under surface: Green Group 138A and 138B and commonly with extensions on three sepals (as illustrated). Commonly two sepals lack extensions.

*Buds.*—Shape: conical. Size: large. Length: approximately 5.5 cm. on average. Color upon opening: Upper surface: Red Group 46A. Under surface: Red Group 53A.

*Flower.*—Shape: with a high center. Diameter: commonly approximately 10.5 cm. on average. Color (when opening begins): Upper surface: near Red Group 46B. Under surface: near Red Group 53B. Color (when blooming): Upper surface: near Red Group 45B. Under surface: near Red Group 45D. Color (at end of opening): Upper surface: near Red Group 45B. Under surface: near Red Group 45D. Fragrance: none. Lasting quality: approximately 10 to 14 days on the plant and approximately 10 to 12 days when cut and placed in a vase. Petal number: commonly approximately 30 to 35 on average. Petal shape: rounded at the base with a reflexed tip. Petal drop: very good, the petals commonly detach cleanly. Stamen number: approximately 95 on average. Anthers: orange in coloration. Filaments: pinkish in coloration. Pollen: formed in abundance, possesses excellent viability, and Yellow Group 11A in coloration. Pistils: approximately 105 on average. Stigmas: pale yellow in coloration. Styles: pale pink in coloration. Receptacle: light green in coloration, smooth, and in longitudinal section in the shape of a funnel.

Development:

*Vegetation.*—Strong.

*Blooming.*—Abundant, and commonly forms approximately 140 to 160 blooms per square meter per year under standard greenhouse growing conditions.

*Aptitude to bear fruit.*—Very good.

*Resistance to diseases.*—Excellent especially with respect to Downey Mildew and Botrytis.

I claim:

1. A new and distinct variety of Hybrid Tea rose plant characterized by the following combination of characteristics:

(a) forms large floral buds;

(b) forms attractive high-centered double deep red blossoms with turgescent petals, (c) exhibits an erect growth habit, (d) exhibits excellent disease resistance particularly with respect to Downey Mildew and Botrytis, and (e) is particularly well suited for the production of cut flowers under greenhouse growing conditions;

substantially as herein shown and described.

* * * * *

MEIVANTHOU